United States Patent [19]

Ansmann et al.

[11] Patent Number: 5,762,916
[45] Date of Patent: Jun. 9, 1998

[54] COSMETIC AND/OR PHARMACEUTICAL PREPARATIONS

[75] Inventors: Achim Ansmann, Erkrath; Armin Wadle, Hilden; Eberhard Eilers, Ulm; Heike Thomas, Langenfeld, all of Germany

[73] Assignee: Henkel Kommanditgesellschaft auf Aktien, Duesseldorf, Germany

[21] Appl. No.: 656,342

[22] PCT Filed: Dec. 10, 1994

[86] PCT No.: PCT/EP94/04113

§ 371 Date: Aug. 28, 1996

§ 102(e) Date: Aug. 28, 1996

[87] PCT Pub. No.: WO95/16430

PCT Pub. Date: Jun. 22, 1995

[30] Foreign Application Priority Data

Dec. 18, 1993 [DE] Germany ............ 43 43 431.2

[51] Int. Cl.⁶ ............ A61K 7/48; A61K 47/42; A61K 38/01
[52] U.S. Cl. ............ 424/70.14; 424/401; 424/70.11; 424/74
[58] Field of Search ............ 424/401, 70.11, 424/70.14, 74, 195.1

[56] References Cited

U.S. PATENT DOCUMENTS

| | | | |
|---|---|---|---|
| 4,406,833 | 9/1983 | Boehme et al. | 260/123.7 |
| 4,705,682 | 11/1987 | Moeller et al. | 424/70 |
| 5,071,960 | 12/1991 | Turowski et al. | 530/356 |
| 5,458,881 | 10/1995 | Berger et al. | 424/401 |

FOREIGN PATENT DOCUMENTS

| | | |
|---|---|---|
| 895719 | 7/1983 | Belgium. |
| 203 418 | 12/1986 | European Pat. Off.. |
| 417 619 | 3/1991 | European Pat. Off.. |
| 35 127 43 | 10/1986 | Germany. |
| WO 92/21318 | 12/1992 | WIPO. |

OTHER PUBLICATIONS

J.Am.Oil.Chem. soc. 59, 217 (1982).
Kosmetische Färbemittel, Verlag Chemie, Weinheim, 1984.

Primary Examiner—Nathan M. Nutter
Attorney, Agent, or Firm—Ernest G. Szoke; Wayne C. Jaeschke; Real J. Grandmaison

[57] ABSTRACT

A cosmetic or pharmaceutical composition containing an emulsifier comprising a highly acylated protein fatty acid condensate having a total nitrogen content, based on the acylation product, of 1.8 to 4.10% by weight.

14 Claims, No Drawings

COSMETIC AND/OR PHARMACEUTICAL PREPARATIONS

BACKGROUND OF THE INVENTION

1. Field of the Invention

This invention relates to cosmetic and/or pharmaceutical preparations containing highly acylated protein hydrolyzates as emulsifiers and to the use of these substances as emulsifiers for the preparations mentioned.

1. Discussion of Related Art

Acylation products of protein hydrolyzates, so-called protein fatty acid condensates, are anionic surfactants which are used, for example, in water-containing cosmetic preparations (hair shampoos etc.) by virtue of their good cleaning performance and their particular compatibility with the skin. Information on the properties of this class of surfactants can be found in the articles by G. Schuster and H. Modde in Parf. Kosm. 45, 337 (1964) and by O. J. Muscio et al. in J. Am. Oil. Chem. Soc. 59, 217 (1982).

Whereas, therefore, protein fatty acid condensates are distinguished by excellent properties in purely aqueous systems, their use in conjunction with oils is generally not possible. Emulsions, especially o/w emulsions, containing acylated protein hydrolyzates have a tendency to thicken and separate with increasing storage.

Accordingly, the problem addressed by the present invention was to provide emulsions containing acylated protein hydrolyzates which would be stable and would have a constant viscosity, even in the event of prolonged storage.

DESCRIPTION OF THE INVENTION

The present invention relates to cosmetic and/or pharmaceutical preparations which are characterized in that they contain as emulsifiers highly acylated protein fatty acid condensates with a total nitrogen content, based on the acylation products, of 1.8 to 4.1% by weight.

It has surprisingly been found that protein hydrolyzates exhibiting excellent emulsifier properties are obtained by increasing the degree of acylation which can be determined through the reduction in the total nitrogen content. The emulsions prepared using these substances are stable in storage and have a constant viscosity. It has proved to be of particular advantage to use protein fatty acid condensates based on vegetable raw materials, more especially soya protein.

Protein Base

As already mentioned, protein fatty acid condensates are known substances. The new highly acylated products are also normally produced from animal or vegetable proteins, for example collagen or keratin and preferably almond protein, wheat protein, potato protein and, in particular, soya protein, which are subjected to acidic, alkaline and/or enzymatic hydrolysis and thereafter have an average molecular weight in the range from 600 to 4,000 and preferably in the range from 2,000 to 3,500.

Production of the Highly Acylated Protein Fatty Acid Condensates

To produce highly acylated protein fatty acid condensates by acidic hydrolysis, dilute sulfuric acid, for example, is added to the starting protein which is then hydrolyzed for 8 to 10 h at 85° to 95° C. On completion of hydrolysis, it is advisable to add aqueous calcium hydroxide solution to the reaction mixture so that the polypeptides are converted into the calcium salts and the hydrolyzed material is precipitated as calcium sulfate. The dispersion is then filtered, a clear solution of calcium peptides being obtained. This solution can be concentrated by evaporation and then directly acylated with fatty acid chlorides. If sodium or potassium salts, for example, are to be produced instead of the calcium salts, it is advisable to treat the calcium peptide solution with soda or potash before the Schotten-Baumann reaction, to filter off the calcium carbonate precipitated and further to process the alkali metal peptides instead of the calcium peptides.

To produce highly acylated protein fatty acid condensates by alkaline hydrolysis, an aqueous calcium hydroxide dispersion is added to the starting material which is then hydrolyzed for 6 to 10 h at 85° to 95° C. and the hydrolyzed material is filtered from the residue. The filtrate contains the calcium peptides which may then be acylated with the fatty acid chlorides. In this case, too, the corresponding alkali metal peptides may be obtained by reprecipitation with soda or potash.

For the actual Schotten-Baumann acylation, the peptide solution is normally introduced first and alkalized, after which fatty acid chloride is run in at a temperature of 40° to 60° C. in such a quantity that a total nitrogen content of 1.8 to 4.1 and, more particularly, 2.0 to 3.5 is obtained in the end product. The calculation of the necessary quantity is dependent upon the average molecular weight of the protein hydrolyzate and may readily be carried out by the expert without any need for inventive activity. The hydrochloric acid released during the condensation is trapped by addition of alkali. After the fatty acid chloride has been added, the mixture is left reacting for 1 to 2 h, after which the protein fatty acid condensate can be adjusted to the required solids content and pH value.

Fatty Acid Base

The condensates suitable as emulsifiers for the purposes of the invention are, formally, acylation products of protein hydrolyzates with aliphatic fatty acids corresponding to formula (I):

$$R^1CO—OH \qquad (I)$$

in which $R^1CO$ is an aliphatic acyl radical containing 6 to 22 and preferably 12 to 18 carbon atoms. As already mentioned, however, the fatty acyl radical is introduced into the condensates through the fatty acid chlorides and not through the fatty acids. When, therefore, the fatty acids from which the protein fatty acid condensates can be derived are referred to in the following, the technical teaching of using the corresponding fatty acid chlorides for their production is associated with the corresponding references.

Examples of fatty acids from which the protein fatty acid condensates may be formally derived are caproic acid, caprylic acid, 2-ethylhexanoic acid, isononanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtainable, for example, by the pressure hydrolysis of fats and oils or by the reduction of aldehydes from Roelen's oxo synthesis.

The protein fatty acid condensates may be used in the form of their alkali metal, alkaline earth metal and/or ammonium salts, preferably as sodium, magnesium and/or calcium salts.

Cosmetic and Pharmaceutical Preparations

The cosmetic and pharmaceutical preparations according to the invention may contain the highly acylated protein fatty acid condensates in quantities of 0.5 to 5% by weight and preferably in quantities of 1 to 4% by weight, based on the preparations.

In one preferred embodiment of the invention, polyols, for example ethylene glycol, diethylene glycol, triethylene glycol, propylene glycol, dipropylene glycol, technical oligoglycerol mixtures with an average degree of self-condensation of 1.5 to 10, trimethylol propane, pentaerythritol, dipentaerythritol, alkyl oligoglucosides based on fatty alcohols containing 8 to 18 carbon atoms, sugar alcohols, such as mannitol or sorbitol, carbohydrates, such as glucose for example, or amino sugars, such as glucamine or N-methyl glucamide for example, are added to the highly acylated protein fatty acid condensates. Glycerol is preferably used as the polyol. The preparations according to the invention may contain the polyols suitable as co-emulsifiers in quantities of 2 to 15% by weight and preferably in quantities of 5 to 10% by weight, based on the preparations.

The cosmetic and/or pharmaceutical preparations may contain, for example, emulsifiers, oil components, fats and waxes, thickeners, biogenic agents, film formers, fragrances, dyes, pearlescers, preservatives and pH regulators as further ingredients.

Suitable superfatting agents are such substances as, for example, polyethoxylated lanolin derivatives, lecithin derivatives and fatty acid alkanolamides, the latter also serving as foam stabilizers. Suitable thickeners are, for example, crosslinked polyacrylic acids and derivatives thereof, polysaccharides, more especially xanthan gum, guar guar, agar agar, alginates and tyloses, carboxymethyl cellulose and hydroxyethyl cellulose, relatively high molecular weight polyethylene glycol monoesters and diesters of fatty acids, polyacrylates, polyvinyl alcohol and polyvinyl pyrrolidone while suitable consistency regulators are fatty acids, fatty alcohols and monoglycerides. In the context of the invention, biogenic agents are, for example, plant extracts, protein hydrolyzates and vitamin complexes. Standard film formers are, for example, polyvinyl pyrrolidone, vinyl pyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, also fatty acids and fatty acid monoglycol esters. The dyes used may be any of the substances suitable and permitted for cosmetic purposes as listed, for example, in the publication "Kosmetische Färbemittel" of the Farbstoffkommission der Deutschen Forschungsgemeinschaft, published by Verlag Chemie, Weinheim, 1984. These dyes are typically used in concentrations of 0.001 to 0.1% by weight, based on the mixture as a whole.

Commercial Applications

Highly acylated protein fatty acid condensates with a total nitrogen content of 1.8 to 4.1% by weight have excellent emulsifier properties. They may be used to prepare storage-stable emulsions with a constant viscosity. Known protein fatty acid condensates with low degrees of acylation and a total nitrogen content of more than 4% by weight are demonstrably unsuitable as emulsifiers.

Accordingly, the present invention relates to the use of the highly acylated protein fatty acid condensates mentioned as emulsifiers for the production of cosmetic and/or pharmaceutical preparations.

The following Examples are intended to illustrate the invention without limiting it in any way.

EXAMPLES

I. Protein Fatty Acid Condensates Used

A1) Potassium salt of an acylation product of animal collagen (average molecular weight 2,500) with $C_{12/14}$ cocofatty acid A2) Potassium salt of an acylation product of soya protein (average molecular weight 3,000) with $C_{12/14}$ cocofatty acid B1) Potassium salt of an acylation product of animal collagen (average molecular weight 3,000) with $C_{12/14}$ cocofatty acid.

The characteristic data of the three products are set out in Table 1 below:

TABLE 1

| | Characteristic Data of the Products | | |
|---|---|---|---|
| Product | Lipid Extract % by weight | Fatty Acid in the Lipid Extract % by weight | Total Nitrogen % by weight |
| A1 | 19.1 | 53.8 | 2.6 |
| A2 | 17.1 | 50.0 | 3.5 |
| B1 | 18.6 | 19.1 | 5.0 |

Products A1 and A2 correspond to the invention while product B1 is intended for comparison.

II. Stability Tests

The following emulsions were evaluated for viscosity and stability after storage for 1 to 12 weeks at 20° C. The results are set out in Table 2 below:

TABLE 2

| | Storage Stability; Percentages as % by Weight | | |
|---|---|---|---|
| | | Examples | |
| Components | 1 | 2 | C1 |
| A1 | 3.5% | — | — |
| A2 | — | 3.5% | — |
| B1 | — | — | 3.5% |
| Cetiol ® LC | 10.0% | 10.0% | 10.0% |
| Cetiol ® OE | 5.0% | 5.0% | 5.0% |
| Cutina ® GMS | 7.0% | 7.0% | 7.0% |
| Lanette ® O | 2.0% | 2.0% | 2.0% |
| Glycerol (86% by weight) | 3.0% | 3.0% | 3.0% |
| Water | 69.5% | 69.5% | 69.5% |
| Viscosity* (1 week) | 4000 | 4000 | 7200 |
| Viscosity* (8 weeks) | 4400 | 4100 | 9600 |
| Stability (12 weeks) | Stable | Stable | Unstable |

*Brookfield viscosity, spindle 5, 10 r.p.m., [mPas]

III. Formulation Examples (Water to 100% by Weight)

Example 3

Day Care Lotion

| | |
|---|---|
| A1 | 2.0% by weight |
| Cetiol ® 868 | 7.0% by weight |
| Cutina ® GMS | 5.0% by weight |
| Cutina ® CP | 1.0% by weight |
| Lanette ® O | 1.0% by weight |
| Novata ® AB | 1.0% by weight |
| Myritol ® GTEH | 7.0% by weight |
| Glycerol (86% by weight) | 5.0% by weight |
| Carbopol ® 981 (2% by weight) | 10.0% by weight |

Example 4

Sunscreen Lotion

| | |
|---|---|
| A2 | 1.5% by weight |
| Cetiol® S | 8.0% by weight |
| Eutanol® G | 2.0% by weight |
| Lanette® O | 1.0% by weight |
| Novata® AB | 1.0% by weight |
| Vitamin E | 3.0% by weight |
| Shea butter | 1.0% by weight |
| Titanium dioxide | 2.0% by weight |
| Cyclomethicone | 6.0% by weight |
| Neo Heliopan® BB | 1.5% by weight |
| Neo Heliopan® E 1000 | 1.0% by weight |
| Neo Heliopan® Hydro | 1.0% by weight |
| Carbopol® 981 (2% by weight) | 20.0% by weight |
| Ethanol | 5.0% by weight |

IV. Ingredients Used

TABLE 3

**Ingredients Used (*)**

| Name | Manuf. | | CTFA Registration |
|---|---|---|---|
| Carbopol | 981 | Goodrich | Polyacrylate |
| Cetiol | LC | Henkel | Coco-Caprylate/Caprate |
| | OE | | Dicaprylether |
| | S | | Dioctylcyclohexane |
| | 868 | | Octylstearate |
| Cutina | CP | Henkel | Cetyl palmitate |
| | GMS | | Glycerol stearate |
| Eutanol | G | Henkel | Octyldodecanol |
| Lanette | O | Henkel | Cetearylalcohol |
| Neo Heliopan | B | Haarmann | UV Absorbers |
| | E 1000 | & | |
| | Hydro | Reimer | |
| Novata | AB | Henkel | Coco glycerides |
| Myritol | GTEH | Henkel | Glyceryl trioctanoate |

(*) The names shown are registered trademarks

What is claimed is:

1. A cosmetic or pharmaceutical composition containing an emulsifier comprising a highly acylated protein fatty acid condensate having a total nitrogen content, based on the acylation product, of 1.8 to 4.1% by weight.

2. A composition as in claim 1 wherein said acylation product is based upon a protein hydrolyzate selected from the group consisting of soya protein, almond protein, wheat protein and potato protein hydrolyzates.

3. A composition as in claim 1 wherein said acylated protein fatty acid condensate has an average molecular weight of 600 to 4,000.

4. A composition as in claim 1 wherein said acylated protein fatty acid condensate is obtained with a fatty acid corresponding to formula (I)

$$R^1CO\text{---}OH \tag{I}$$

in which $R^1CO$ is a $C_{6-22}$ aliphatic acyl radical.

5. A composition as in claim 1 wherein said acylated protein fatty acid condensate is present as a salt selected from the group consisting of alkali metal, alkaline earth metal and ammonium salts.

6. A composition as in claim 1 wherein said acylated protein fatty acid condensate is present in an amount of 0.5% to 5% by weight, based on the weight of said composition.

7. A composition as in claim 1 further containing 2% to 15% by weight of a polyol co-emulsifier, based on the weight of said composition.

8. The process of providing a storage-stable emulsified cosmetic or pharmaceutical composition comprising adding to said composition an emulsifier comprising a highly acylated protein fatty acid condensate having a total nitrogen content, based on the acylation product, of 1.8 to 4.1% by weight.

9. A process as in claim 8 wherein said acylation product is based upon a protein hydrolyzate selected from the group consisting of soya protein, almond protein, wheat protein and potato protein hydrolyzates.

10. A process as in claim 8 wherein said acylated protein fatty acid condensate has an average molecular weight of 600 to 4,000.

11. A process as in claim 8 wherein said acylated protein fatty acid condensate is obtained with a fatty acid corresponding to formula (I)

$$R^1CO\text{---}OH \tag{I}$$

in which $R^1CO$ is a $C_{6-22}$ aliphatic acyl radical.

12. A process as in claim 8 wherein said acylated protein fatty acid condensate is present as a salt selected from the group consisting of alkali metal, alkaline earth metal and ammonium salts.

13. A process as in claim 8 wherein said acylated protein fatty acid condensate is present in an amount of 0.5% to 5% by weight, based on the weight of said composition.

14. A process as in claim 8 further including adding to said composition 2% to 15% by weight of a polyol co-emulsifier, based on the weight of said composition.

* * * * *